United States Patent [19]

Masson

[11] 4,064,425

[45] Dec. 20, 1977

[54] LIGHTING PROJECTOR

[75] Inventor: André A. Masson, Saint-Heand, France

[73] Assignee: Etablissements Pierre Angenieux, Paris, France

[21] Appl. No.: 759,400

[22] Filed: Jan. 14, 1977

[30] Foreign Application Priority Data

Jan. 21, 1976 France ................................ 76.01538

[51] Int. Cl.[2] ................................................ A61B 1/06

[52] U.S. Cl. ........................................................ 362/33

[58] Field of Search .............................. 240/1.4, 41.15

[56] References Cited

U.S. PATENT DOCUMENTS

| | | | |
|---|---|---|---|
| 1,987,019 | 1/1935 | Logan | 240/1.4 |
| 3,225,184 | 12/1965 | Reiber | 240/1.4 |
| 3,437,803 | 4/1969 | Seitz et al. | 240/1.4 |

*Primary Examiner*—Leland A. Sebastian
*Attorney, Agent, or Firm*—Michael J. Striker

[57] ABSTRACT

A lighting projector, notably for surgical theatres, comprising a central case enclosing light sources, and radial basic elements of tubular configuration provided with optical means for reflecting the light rays received from said sources towards the area to be illuminated, said means comprising notably a first mirror and a second mirror, the latter being disposed on the path of the light rays and capable of returning one portion thereof towards the area to be illuminated while allowing the other fraction to pass towards said first mirror located at the outer end of the element.

3 Claims, 4 Drawing Figures

LIGHTING PROJECTOR

BACKGROUND OF THE INVENTION

1. Field of the Invention

The present invention relates to a lighting projector of the type disclosed in the U.S. Pat. No. 3,848,119 and intended more particularly for surgical theatres or rooms.

With this specific object in view, this lighting projector is designed with the purpose of eliminating cast shadows and providing a uniform illuminated field or area of high luminous intensity or candlepower, with a cold light and a minimum cross-sectional obstruction area.

For this purpose, the projector according to the above-mentioned U.S. Pat. No. 3,848,119 consisted of a plurality of basic elements extending radially outwards from a central point, each element comprising in turn, in the direction from the centre to its tip or outer end, a light source, a frosted zone or surface located in close vicinity of said light source, and an optical system adapted to form the image of said frosted zone on the plane to be illuminated after reflecting the light beam from said source onto an inclined mirror.

Thus, the field or plane contemplated is illuminated by the light beam issuing from the various basic elements constituting the projector, the mirrors being properly oriented so that the axes of said light beams will converge towards a same area or spot corresponding to the centre of the field to be illuminated. All the light sources are grouped at or near the centre of the projector and may be mounted within a single casing, thus facilitating the dissipation of the heat generated by said light sources.

DESCRIPTION OF THE INVENTION

It is the essential object of the present invention to improve the properties of a projector of the above-described type by increasing the number of light beams, however without increasing the number of basic elements of the projector. In fact, it is desirable that this number remains as low as possible in order to minimize the cross-section obstruction area, in order not to interfere with the ventilation of the room in which the projector is installed, which is particularly important in the specific case of an operation or surgical theatre in which a lamellar air flow is maintained.

Now, the scopes contemplated herein are obviously of contradictory nature. Nevertheless, the desired results are achieved with the new embodiment of the lighting projector proposed in the form of the present invention.

For this purpose, each basic element of the lighting projector comprises, upstream of the reflection mirror adjacent the tip of the element, an additional reflection mirror capable of returning one portion of the light rays towards the plane to be illuminated while allowing the remaining fraction of said light rays to flow towards the reflection mirror located at the tip, or outer end, of the element concerned.

Thus, each element of the lighting projector produces two light beams directed towards the field to be illuminated. This further reduces the possibility of creating cast shadows, without increasing the total obstruction surface area in the air, which is caused by the presence of the projector itself.

A typical embodiment of this lighting projector will now be described with reference to the attached drawing, in which:

DESCRIPTION OF THE PREFERRED EMBODIMENT

As in the case of the lighting projector disclosed in the aforesaid U.S. Pat. No. 3,848,119, this lighting projector comprises a plurality of basic elements disposed radially about a central casing 5, but in the present case the basic elements 1, 2, 3 and 4 of this lighting projector are four in number and distributed by pairs, the two elements of a same pair being disposed in mutual axial alignment on either side of said central casing 5.

Each basic element comprises a tubular casing enclosing the optical components of the element and is rigid with the central casing 5. However, in the present example, instead of comprising an individual light source for each base element, the projector according to the instant invention comprises a light source common to each pair of basic elements disposed in relative axial alignment, respectively. More particularly, in this embodiment two light sources *6a* and *6b* are provided instead of four in the aforesaid patent. In this invention, the first light source *6a* is common to both elements 1 and 3, while the other light source *6b* is common to the other pair of elements 2 and 4.

Figure 1:
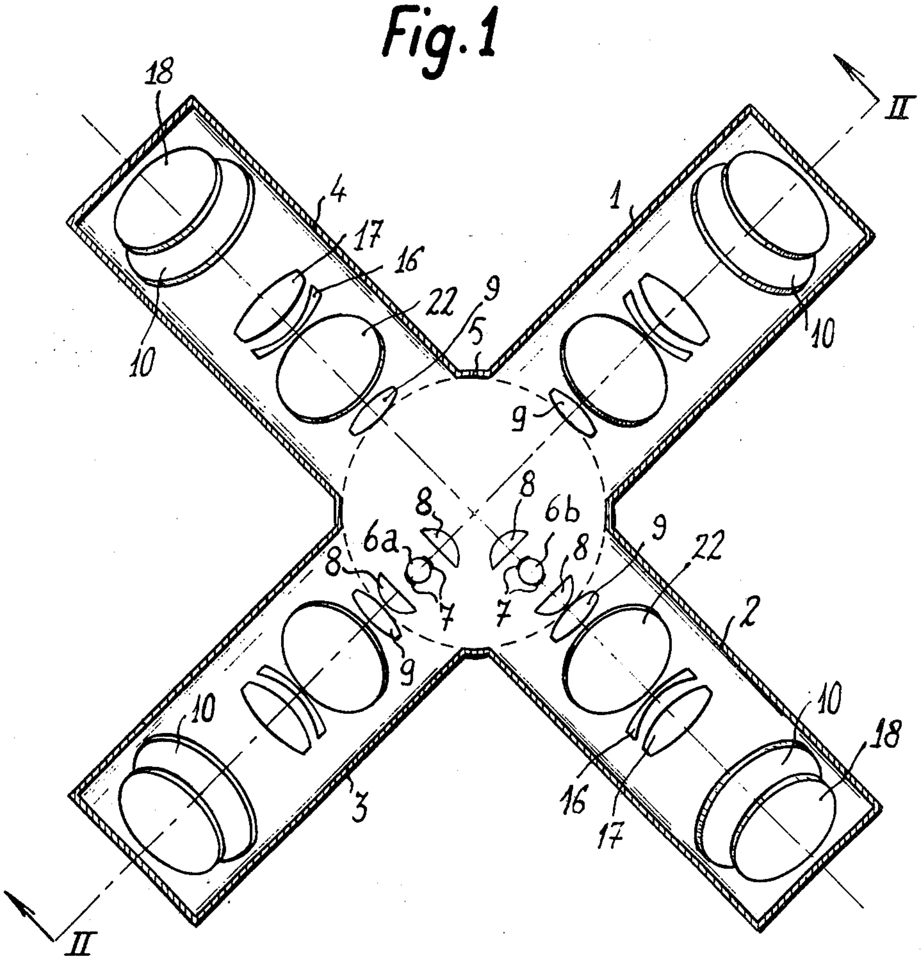
FIG. 1 is a diagrammatic view of the lighting projector shown in section taken along a horizontal plane.

As clearly shown in FIG. 1, the first light source *6a* is disposed on the side of one of the two basic elements of the corresponding pair, namely the adjacent element 3. The other light source *6b* is adjacent another basic element 2.

On either side of each light source a pair of frosted zones 7 located in close vicinity thereof are provided. In actual practice, each frosted zone may be formed on the transparent envelope of the corresponding electric bulb *6a* or *6b*, said zones being obtained by grinding or frosting the glass or quartz bulb constituting said envelope.

Due to this eccentric arrangement of the two light sources *6a* and *6b*, the paths of the light beams formed thereby in a same pair of aligned basic elements have unequal lengths.

Each basic element of the projector according to this invention comprises a condenser-type optical system consisting of a pair of lenses 8 and 9. Due to the specific arrangement contemplated for the light sources, the disposition of the two corresponding lenses differs in the two component elements of a same pair (see FIG. 1) on account of the difference between the paths of the light beams.

At the outer end, each basic element comprises a reflection mirror 10 inclined towards an aperture 11 formed in the wall of the tubular casing of the relevant element. The angle of inclination of said mirrors 10 thus provided at the tip of the various elements 1, 2, 3 and 4 is such that the light beams 12 issuing therefrom converge towards the field or area 13 to be illuminated. The axes 14 of these four light beams are disposed on generatrices of a common cone having its vertex 15 located centrally of the illuminated field 13.

Upstream of the reflection mirror 10 each basic element of this lighting projector comprises an optical system adapted to form the image of the corresonding frosted zone 7 in the plane 13 of the illuminated field, after its reflection by said mirror 10. In the embodiment illustrated, this optical system comprises a pair of lenses 16 and 17.

Figure 2:
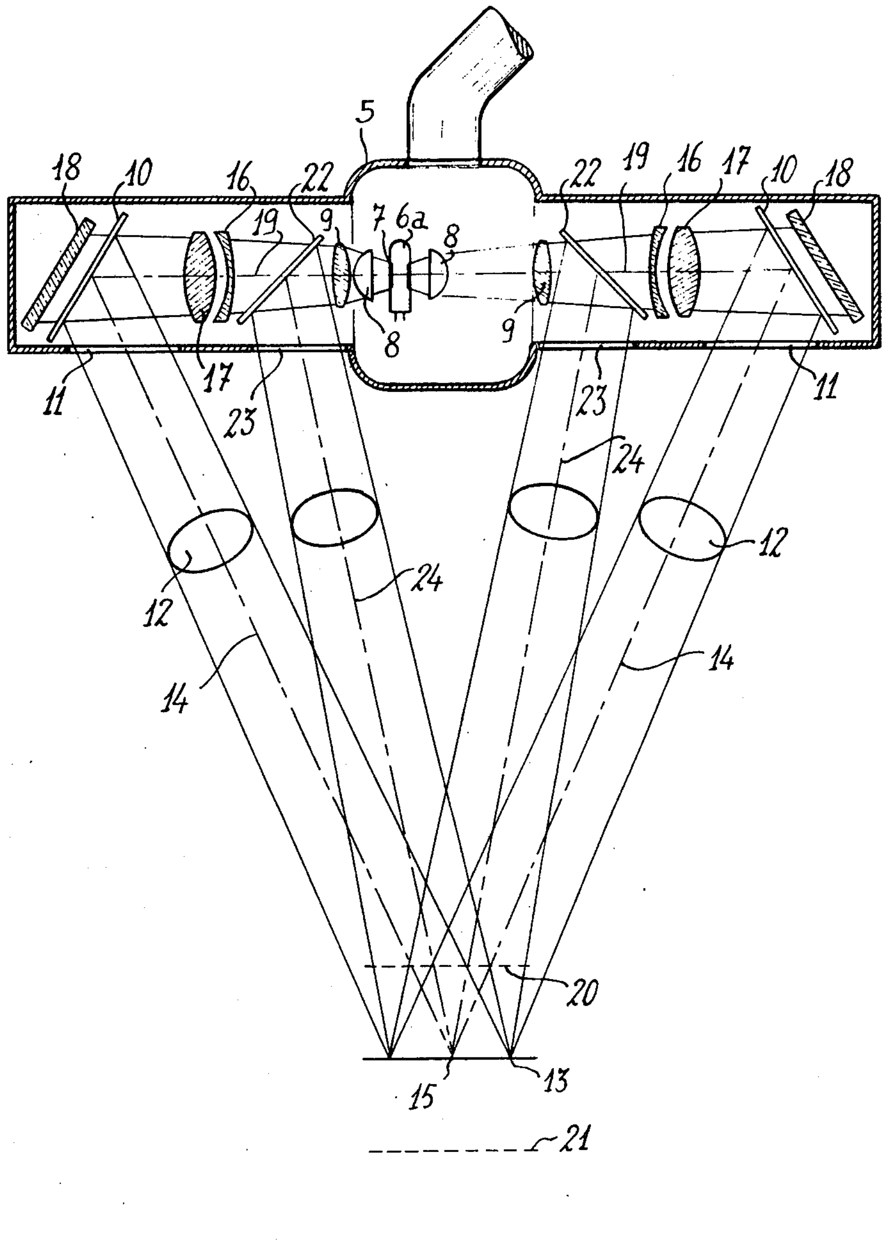
FIG. 2 is a fragmentary vertical section taken along the line II—II of FIG. 1, this view constituting a clear explanatory diagram concerning the mode of operation of one of the basic elements of the lighting projector.
Figure 4:
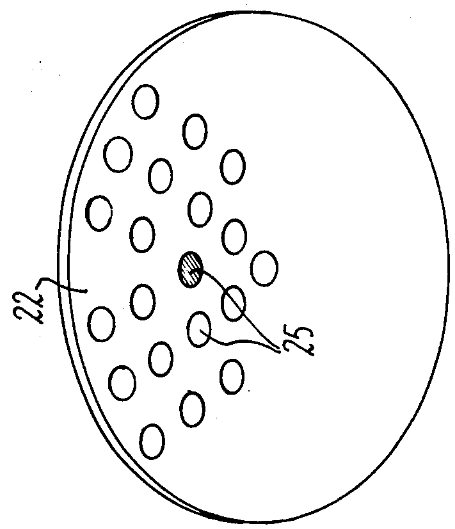
FIG. 4 is a plane view from above of the same additional mirror.
Figure 3:
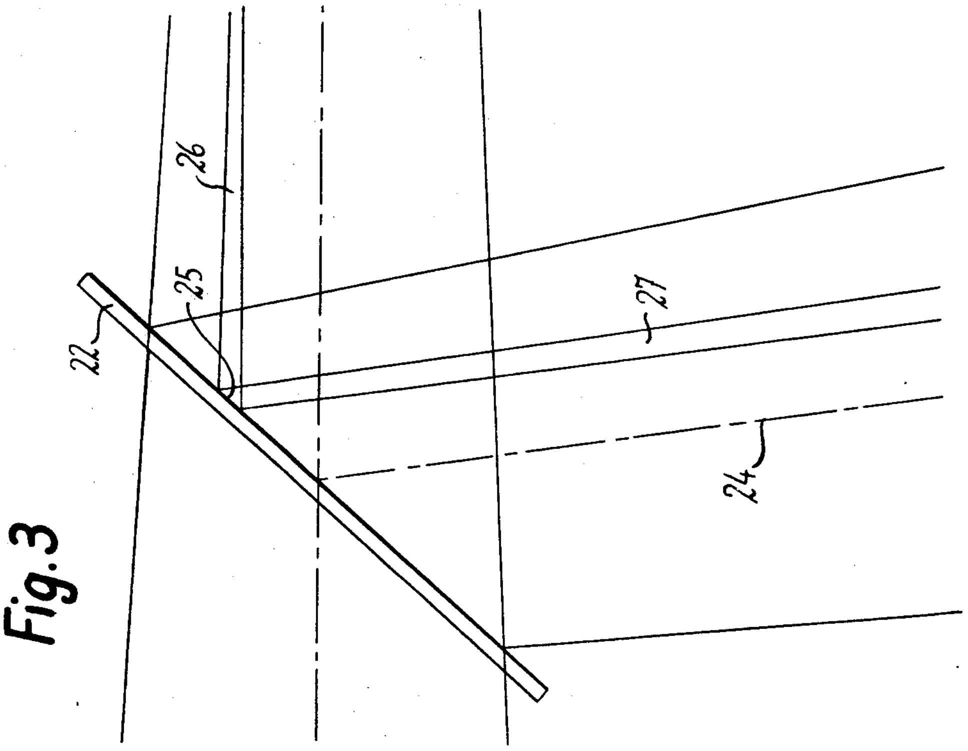
FIG. 3 is a diagrammatical view illustrating the mode of operation of the additional reflection mirror incorporated in said basic element.

The reflecting surface of mirror 10 comprises a complex system of thin interferential layers whereby only the light rays can be reflected while the heat rays are allowed to pass therethrough. Thus, these heat rays pass each through said mirrors 10 and are received by an end element 18 acting as a radiator so as to dissipate said heat rays. Therefore, only the light energy is reflected towards the field 13 to be illuminated. Preferably, the inclination of the reflection mirror 10 is adjustable in relation to the axis 19 of the initial light beam, so that the light energy can be focused onto an illuminated plane 13 which varies in position between two endmost parallel planes 20 and 21 (FIG. 2).

According to an original feature characterising the lighting projector according to this invention, each basic element thereof comprises an additional reflection mirror 22 interposed between the optical condensing system 8, 9 and the optical lens system 16, 17. This additional mirror is inclined towards an aperture 23 formed in the lower portion of the tubular casing of the corresponding element. Moreover, its inclination is such that the axis 24 of the light beam reflected by said mirror is focused onto the field 13 to be illuminated (FIG. 2).

However, the mirrors 22 of the various elements 1, 2, 3 and 4 of the instant projector have a specific design in that they reflect only one portion of the light rays while allowing the remaining portion thereof to pass so that this fraction can strike the corresonding endmost reflection mirror 10. For this purpose, each mirror 22 consists of a plate of glass or other suitable transparent material carrying a series of reflecting areas or zones 25 separated from one another by completely transparent areas permitting the free passage of the light rays, and also of the heat rays, in the direction of the corresponding endmost mirror 10. This constitutes so to say a patterned or raster-type reflecting surface.

However, the zones 25 are made in the same fashion as the reflecting surfaces of the endmost mirrors 10. In fact, each zone 25 comprises a complex assembly of thin interferential layers reflecting only the light rays while permitting the passage of the heat rays, so that said heat rays eventually strike the endmost element 18 acting as a heat-dissipating radiator.

Under these conditions, considering now a beam 26 of light and heat rays issuing from the corresponding light source and impinging against one of the reflecting zones 25 of mirror 22, the corresponding light rays are reflected downwards in the form of a light beam 27. On the other hand, the heat rays contained in said beam 26 pass the mirror 22 and then through the endmost mirror 10 of the corresponding element, until they strike the radiator 18.

Therefore, each additional mirror 22 is adapted to split simultaneously the incoming rays at two different levels, so that:

at a spectral level, the reflecting zones 25 separate the light rays from the heat rays and reflect only the light spectrum while permitting the passage of the heat radiation through said zones, and at a space level, the transparent areas separating the reflecting zones 25 permit the free passage of both light rays and heat rays received by said zones 25.

The amount of light eventually received by the field 13 to be illuminated is substantially the same as if said additional reflection mirror 22 had not been provided, however, the number of light beams striking said field under different angles is doubled. Consequently, this will assist in further reducing to a considerably greater extent the risk of having cast shadows, without inasmuch increasing the number of basic elements of the lighting projector. On the other hand, as already mentioned in the foregoing, an essential advantage characterising this invention is that the lighting projector constituting the subject-matter thereof comprises a reduced number of light sources and nevertheless a sufficient number of basic elements.

Of course, the lighting projector according to this invention should not be construed as being strictly limited by the specific form of embodiment shown and described herein, since various modifications and variations may be brought thereto without departing from the basic principles of the invention as set forth in the appended claims.

What is claimed as new is:

1. A lighting projector comprising a star-shaped arrangement of a plurality of basic elements of elongated configuration, rigid with a case disposed in the central portion of said projector and radiating therearound, a plurality of light sources disposed in said central portion, each basic element comprising a first reflecting mirror located adjacent its outer end, opposite said central case and inclined towards the surface to be illuminated, an optical system disposed in the path of the light beam issuing from one of said light sources and directed towards a first reflection mirror disposed at the outer end of the corresponding basic element, said optical system being adapted to form the image of the corresponding light source onto the surface to be illuminated after causing said image to be reflected by said mirror, a second reflecting mirror also disposed in the path of said light beam and capable of returning one portion of the light rays towards the plane to be illuminated while allowing the other fraction of said light rays to pass towards said first reflection mirror located at the end of the element concerned.

2. Lighting projector as recited in claim 1, wherein said second reflection mirror of each basic element comprises a series of reflecting zones separated by transparent areas.

3. Lighting projector as recited in claim 1, wherein said second reflection mirror of each basic element comprises a series of reflecting zones separated by transparent areas, said reflecting zones consisting each of a complex system of thin interferential layers for reflecting only the light energy and not the heat energy received from said light source.

* * * * *